(12) United States Patent
Yoon (10) Patent No.: US 8,951,269 B2
(45) Date of Patent: Feb. 10, 2015

(54) SURGICAL SUTURE APPARATUS HAVING SEWING FUNCTION

(75) Inventor: Sang Jin Yoon, Seoul (KR)

(73) Assignee: Rimscience Co., Ltd., Seoul (KR)

( * ) Notice: Subject to any disclaimer, the term of this patent is extended or adjusted under 35 U.S.C. 154(b) by 111 days.

(21) Appl. No.: 13/318,012

(22) PCT Filed: Jun. 24, 2009

(86) PCT No.: PCT/KR2009/003419
§ 371 (c)(1),
(2), (4) Date: Oct. 28, 2011

(87) PCT Pub. No.: WO2010/126197
PCT Pub. Date: Nov. 4, 2010

(65) Prior Publication Data
US 2012/0053601 A1 Mar. 1, 2012

(30) Foreign Application Priority Data
Apr. 28, 2009 (KR) .......................... 10-2009-0037128

(51) Int. Cl.
*A61B 17/04* (2006.01)
*A61B 19/00* (2006.01)

(52) U.S. Cl.
CPC .......... *A61B 17/0491* (2013.01); *A61B 19/2203* (2013.01); *A61B 19/5244* (2013.01)
USPC ........................................................ 606/144

(58) Field of Classification Search
USPC ................. 606/139, 144–150, 222–227, 233; 112/169, 221, 470.12, 259, 117, 112/470.13
See application file for complete search history.

(56) References Cited

U.S. PATENT DOCUMENTS

| 803,508 A | * | 10/1905 | Robb | 112/117 |
| 2,327,353 A | * | 8/1943 | Karle | 606/146 |
| 2,594,534 A | * | 4/1952 | Bell | 112/169 |
| 2,864,327 A | * | 12/1958 | Cole et al. | 112/470.13 |
| 3,745,950 A | * | 7/1973 | Kato | 112/169 |
| 3,834,333 A | * | 9/1974 | Seyama | 112/169 |
| 3,943,864 A | * | 3/1976 | Feighery et al. | 112/7 |
| 4,841,888 A | * | 6/1989 | Mills et al. | 112/169 |

(Continued)

FOREIGN PATENT DOCUMENTS

| EP | 0174843 A2 | 3/1986 |
| JP | 51-020393 | 2/1976 |
| JP | 2007044556 A | 2/2007 |

OTHER PUBLICATIONS

International Search Report for PCT Application No. PCT/KR2009/003419/. Korean Intellectual Property Office. May 11, 2010.

*Primary Examiner* — David Eastwood
(74) *Attorney, Agent, or Firm* — Mayer Brown LLP; Hyunho Park (57) ABSTRACT

The present invention relates to a surgical suture apparatus having a sewing function. In accordance with one aspect of the present invention, there is provided a surgical suture apparatus comprising: a coupling part, a shaft part connected to the coupling part, an operating part, and a suture part connected to the shaft part by way of the operating part, the suture part including a support, a surgical needle and a needle driving part, wherein the surgical needle operates in a direction substantially orthogonal to the support by the needle driving part, and a suture thread from the surgical needle and a suture thread from the support are entangled with each other by the operations.

3 Claims, 5 Drawing Sheets

(56) References Cited

U.S. PATENT DOCUMENTS

| | | | |
|---|---|---|---|
| 5,651,322 A * | 7/1997 | Koike | 112/169 |
| 5,875,726 A * | 3/1999 | Keilmann | 112/470.13 |
| 7,918,170 B2 * | 4/2011 | Myers et al. | 112/117 |
| 2002/0104468 A1 * | 8/2002 | Myers et al. | 112/117 |
| 2004/0092963 A1 * | 5/2004 | Moll et al. | 606/144 |
| 2006/0190032 A1 | 8/2006 | Wales | |
| 2007/0213757 A1 * | 9/2007 | Boraiah | 606/184 |

* cited by examiner

SURGICAL SUTURE APPARATUS HAVING SEWING FUNCTION

PRIORITY

The present application claims priority under 35 U.S.C. §371 to PCT Application PCT/KR2009/003419, filed on Jun. 24, 2009, which claims priority to Korean Patent Application No. 10-2009-0037128, filed on Apr. 28, 2009, the disclosures of which are hereby incorporated by reference in their entireties.

TECHNICAL FIELD

The present invention relates to a surgical suture apparatus having a sewing function. More particularly, the present invention relates to a surgical suture apparatus with which an operator such as a surgeon can suture the tissues of a human body finely, quickly and easily.

BACKGROUND ART

In a surgical operation, it is essential to suture the various tissue layers of a human body such as a serosa, a muscle, a fascia and a skin. The major concerns in this suture process are, by reducing the time taken to suture, to minimize operator fatigue and anesthesia time, to help wound recovery, and to minimize blood loss. In addition, minimizing scars caused due to a surgical operation may be necessary from the viewpoint of beautifying a patient.

DISCLOSURE OF INVENTION

Technical Problem

The conventional suture process has been performed generally in a manner that an operator manually sutures human tissues in need of suturing by using surgical needles and suture threads.

However, according to the conventional suture process based on an operator's manual work, the time for surgery is often extended depending on the operator's skills and experiences for suturing. This may lead to more operator fatigue, longer anesthesia time or more difficult blood management.

Further, though the degree of scars caused due to a suture depends on how uniform and dense the stitches are, the uniformity and density of the stitches cannot be guaranteed with the conventional manual suture.

Technical Solution

It is an object of the present invention to solve the aforementioned problems.

It is another object of the present invention to provide a surgical suture apparatus for enabling an operator to perform a suture finely and easily.

It is yet another object of the present invention to provide a surgical suture apparatus for reducing the time taken to suture.

It is still yet another object of the present invention to provide a surgical suture apparatus for minimizing scars caused due to a suture.

It is still yet another object of the present invention to provide a surgical suture apparatus, connected to an external apparatus such as a surgical robot system with a robot arm, for enabling an operator to perform an automated suture.

Advantageous Effects

In accordance with the present invention, an operator can perform a suture finely and easily.

In accordance with the present invention, the time taken to suture can be reduced.

In accordance with the present invention, scars caused due to a suture can be minimized.

In accordance with the present invention, provided is a surgical suture apparatus, connected to an external apparatus such as a surgical robot system, for enabling an operator to perform an automated suture.

DESCRIPTION OF DRAWINGS

The above objects and features of the present invention will become apparent from the following description of the preferred embodiments given in conjunction with the accompanying drawings, in which.

BEST MODE

Several representative configurations for achieving the aforementioned objects of the present invention are presented as follows.

In accordance with one aspect of the present invention, there is provided a surgical suture apparatus comprising: a coupling part, a shaft part connected to the coupling part, an operating part, and a suture part connected to the shaft part by way of the operating part, the suture part including a support, a surgical needle and a needle driving part, wherein the surgical needle operates in a direction substantially orthogonal to the support by the needle driving part, and a suture thread from the surgical needle and a suture thread from the support are entangled with each other by the operations.

In accordance with another aspect of the present invention, there is provided a surgical suture apparatus comprising: a first coupling part and a second coupling part, a first shaft part connected to the first coupling part and a second shaft part connected to the second coupling part, a first operating part and a second operating part, and a first suture part connected to the first shaft part by way of the first operating part and a second suture part connected to the second shaft part by way of the second operating part, wherein the first suture part includes a surgical needle and a needle driving part, and the second suture part includes a support, and wherein the surgical needle operates in a direction substantially orthogonal to the support by the needle driving part, and a suture thread from the surgical needle and a suture thread from the support are entangled with each other by the operations.

MODE FOR THE INVENTION

In the following detailed description, reference is made to the accompanying drawings that show, by way of illustration, specific embodiments in which the present invention may be practiced. These embodiments are described in sufficient detail to enable those skilled in the art to practice the present invention. It is to be understood that the various embodiments of the present invention, although different, are not necessarily mutually exclusive. For example, a particular feature, structure or characteristic described herein in connection with one embodiment may be implemented within other embodiments without departing from the spirit and scope of the present invention. In addition, it is to be understood that the location or arrangement of individual elements within each disclosed embodiment may be modified without departing from the spirit and scope of the present invention. The following detailed description is, therefore, not to be taken in a limiting sense, and the scope of the present invention is defined only by the appended claims, appropriately interpreted, along with the full range of equivalents to which the claims are entitled. In the drawings, like numerals refer to the same or similar functionality throughout the several views.

The present invention will now be described in more detail, with reference to the accompanying drawings.

Figure 1:
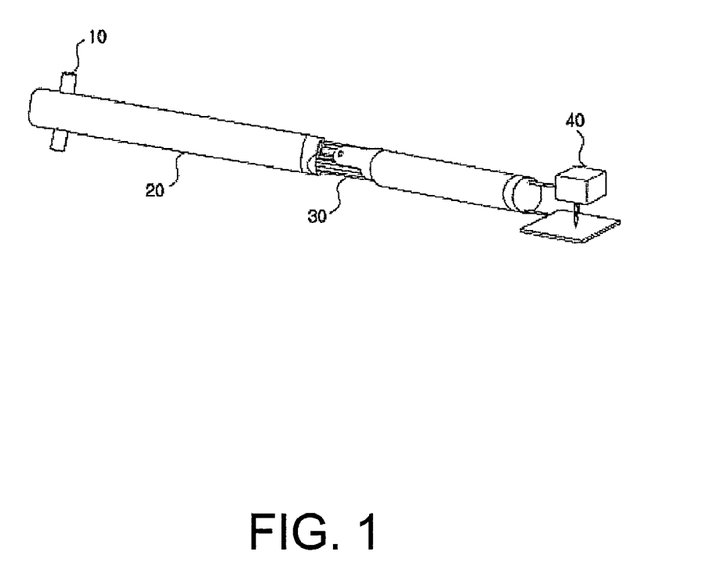
FIG. 1 is a drawing illustrating the overall configuration of the surgical suture apparatus in accordance with one embodiment of the present invention.

FIG. 1 is a drawing illustrating the overall configuration of the surgical suture apparatus in accordance with one embodiment of the present invention.

As shown in FIG. 1, the surgical suture apparatus in accordance with one embodiment of the present invention may include a coupling part 10, a shaft part 20, an operating part 30 and a suture part 40.

In accordance with one embodiment of the present invention, a coupling part 10 enables the surgical suture apparatus to be coupled to an external apparatus such as a surgical robot system with a robot arm.

With regard to connecting a surgical apparatus to a surgical robot system or a robot arm, we may refer to Korean Patent Laid-open Publication No. 2005-100147 (Publication Date: Oct. 18, 2005) and Korean Patent Laid-open Publication No. 2008-89579 (Publication Date: Oct. 7, 2008). Herein, the contents of the above two publications should be regarded as being incorporated into the present specification in their entirety.

In accordance with one embodiment of the present invention, a shaft part 20 may include a shaft, whose one end is connected to a coupling part 10 and other end is connected to an operating part 30. Inside the shaft part 20, control parts such as a wire for controlling the operating part 30 and/or a suture part 40 may be included. Further, the shaft may physically support the surgical suture apparatus in accordance with the present invention.

In accordance with one embodiment of the present invention, an operating part 30 may connect a suture part 40 to a shaft part 20, and adjust the position and the angle of the suture part 40 with regard to the shaft part 20 in response to a predetermined control signal from an external apparatus. The operating part 30 may comprise more than two joint parts for performing a pitch-direction operation and/or a yaw-direction operation as necessary. To configure the operating part 30, any disclosed principle for constructing a joint part of a surgical apparatus may further be employed.

Figure 2:
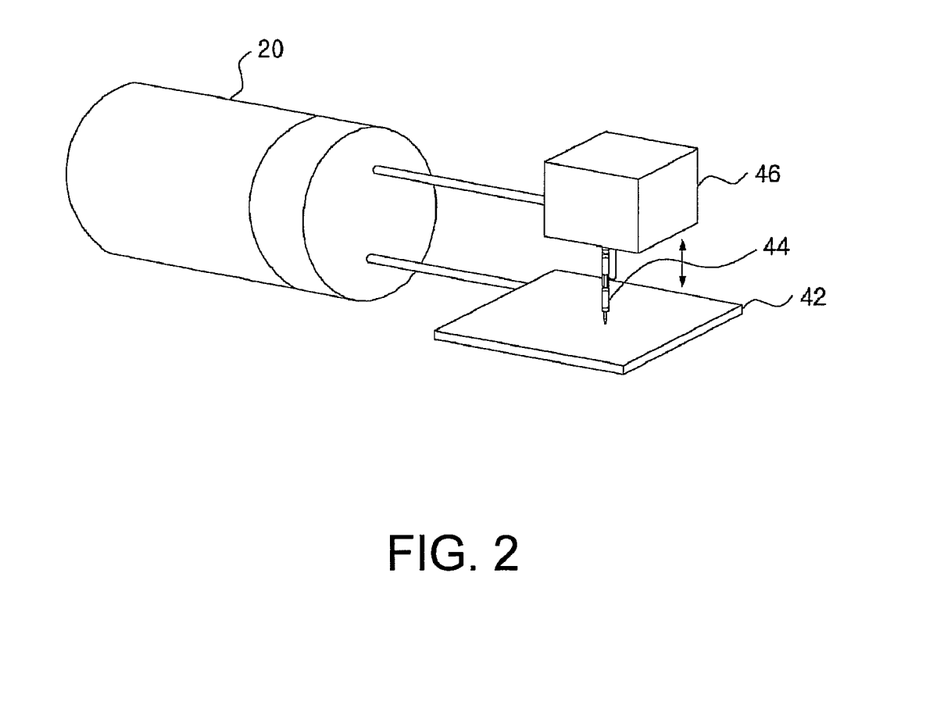
FIG. 2 is a detailed drawing illustrating the configuration of a suture part 40 of the surgical suture apparatus in accordance with one embodiment of the present invention.

A suture part 40 in accordance with several embodiments of the present invention will be described in detail in the following. FIG. 2 is a detailed drawing illustrating the configuration of a suture part 40 of the surgical suture apparatus in accordance with one embodiment of the present invention.

Referring to FIG. 2, a suture part 40 is an element to suture human tissues, and more particularly, may have a lower support 42, a surgical needle 44 and a needle driving part 46 for receiving the surgical needle 44 and actuating the surgical needle 44 in a direction substantially orthogonal to the lower support 42. Hereinafter, it is, for example, explained that a support of the suture part 40 in accordance with the present invention is a lower one, but it is to be understood that a support opposite to a surgical needle 44 may be positioned at an upper location of the surgical needle 44 as necessary.

In accordance with one embodiment of the present invention, a suture part 40 may suture human tissues following the same or similar way that a well-known sewing machine operates, which has been used for cloths for a long time. In other words, human tissues may be sutured by entangling or interlocking a suture thread from a surgical needle 44 with a suture thread from a lower support 42 following the up-and-down movements of the surgical needle 44. Preferably, in this case, it is important that the suture threads from the surgical needle 44 and the lower support 42 are entangled with each other, not tied up. Further, the suture thread used in the surgical suture apparatus in accordance with the present invention may basically be provided from the suture part 40. This suture thread may preferably be a disposable one for sanitation. Likewise, the surgical needle 44 used in the surgical suture apparatus in accordance with the present invention may preferably be a disposable needle module.

In accordance with one embodiment of the present invention, a suture part 40 may actuate a needle driving part 46 based on a control signal inputted from an external apparatus such as a surgical robot system. For example, a surgical needle 44 of a suture part 40 may move in a direction substantially orthogonal to a lower support 42 following an operator's manipulation to the external apparatus.

In this case, the operator may use various options. For example, the operator may choose one of the following options for driving a surgical needle 44 (or a suture part 40) that reflect several basic functions of the well-known sewing machine and are especially advantageous in performing a surgical operation.

1. 3-layer suture: suturing three tissue layers, not only two tissue layers 2. 3-line suture: suturing with three threads hooked by a surgical needle 44

3. 4-line suture: suturing with four threads hooked by a surgical needle 44

4. zigzag suture: suturing with a suture part 40 being controlled to move zigzag 5. parallel suture: suturing two tissue layers, the sides of which contact each other 6. 2-needle suture: suturing by two surgical needles 44

7. elastic suture: suturing with an elastic thread 8. hemming suture: suturing in a manner that a thread is wound up into a spring shape 9. embroidering: embroidering something (e.g., a surgery date or a marking) on a tissue 10. stitching: stitching an object (e.g., an artificial organ) and a tissue so that the object is attached to the tissue 11. blind suture: suturing in a manner that a thread is not seen outside of a tissue 12. overlocking suture: suturing over the edge of one or two tissues for edging, hemming or seaming 13. ligaturing suture: suturing till a blood vessel is tied Further, in accordance with one embodiment of the present invention, an operator may control progress of the suture at a suture part 40. For example, the suture part 40 may be driven as an operator controls progress of the suture by selecting one out of the automatic mode and the semiautomatic mode through an external apparatus. In the automatic mode, the suture part 40 continues to perform a suture in the direction as it has been unless the operator controls to stop the suture. In the semiautomatic mode, the suture part 40 may stop the suture after finishing a designated number of stitchings, even though the operator does not interrupt the suture.

In accordance with one embodiment of the present invention, a gap of two stitches and a suturing speed, which are major factors for various kinds of suturings as described above, may be determined by an operator. Preferably, the gap and/or the suturing speed may be determined by a skilled operator according to the very kind of the tissues (e.g., tissues of a circulatory organ, tissues of a respiratory organ or tissues of a skin) to be sutured. Further, the gap and/or the suturing speed may be determined as an operator selects one out of a few predetermined suturing modes based on the kind of the tissues to be sutured. Further, there would be applied a configuration where, in case the length of the tissues to be sutured is too long, the length of a shaft part 20 is able to increase or decrease as a suture part 40 moves.

The surgical suture apparatus in accordance with the present invention may be unlimitedly applicable to any kind of surgery (e.g., laparotomy). Thus, it may be applicable to invasive surgery such as laparoscopic surgery and endoscopic surgery. In this case, the surgical suture apparatus may be configured differently from what is illustrated in FIG. 1 or FIG. 2. For example, a shaft part 20 may be configured to be suitable (e.g., thinner and longer) for invasive surgery, an operating part 30 may have a plurality of joint parts, or a suture part 40 may be miniaturized. Following one of the above suggestions, the surgical suture apparatus can be inserted easily. Further, an endoscope to secure an operator's view or a pair of tweezers for picking up the human tissues to be sutured may be used together with the surgical suture apparatus in accordance with the present invention.

Figure 3:
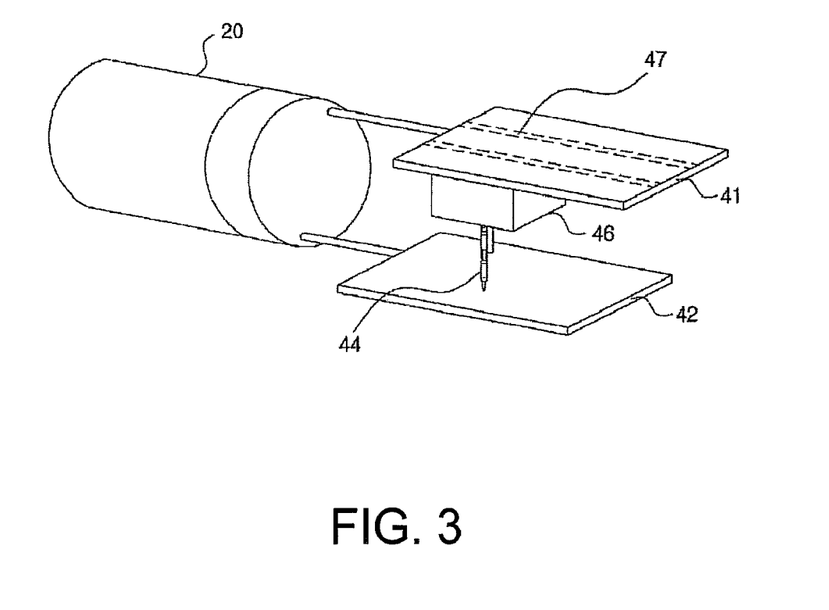
FIG. 3 is a detailed drawing illustrating the configuration of a suture part 40 of the surgical suture apparatus in accordance with another embodiment of the present invention.

In accordance with another embodiment of the present invention, a surgical suture apparatus may include a coupling part 10, a shaft part 20, an operating part 30 and a suture part 40 as described FIG. 2, wherein the shape of the suture part 40 is modified to some extent. FIG. 3 is a detailed drawing illustrating the configuration of a suture part 40 of the surgical suture apparatus in accordance with another embodiment of the present invention.

Referring to FIG. 3, a suture part 40 may include an upper support 41 and a lower support 42, which are opposite to each other, a surgical needle 44, and a needle driving part 46 for receiving the surgical needle 44 and actuating the surgical needle 44 in a direction substantially orthogonal to the lower support 42. Further, the needle driving part 46 may be located at the upper support 41, and configured to move in a predetermined range along the line of a rail 47 located on the upper support 41.

In accordance with the present embodiment, the length of a shaft part 20 may not need to be increased or decreased because the needle driving part 46 moves along the line of the rail 47 and is driven for suturing. This is the difference between the present embodiment and those described above.

In case that the surgical suture apparatus in accordance with the above embodiment is applied to invasive surgery, a problem may arise that a port used for the invasive surgery is required to be larger due to the relatively large widths of the upper support 41 and the lower support 42.

Figure 4:
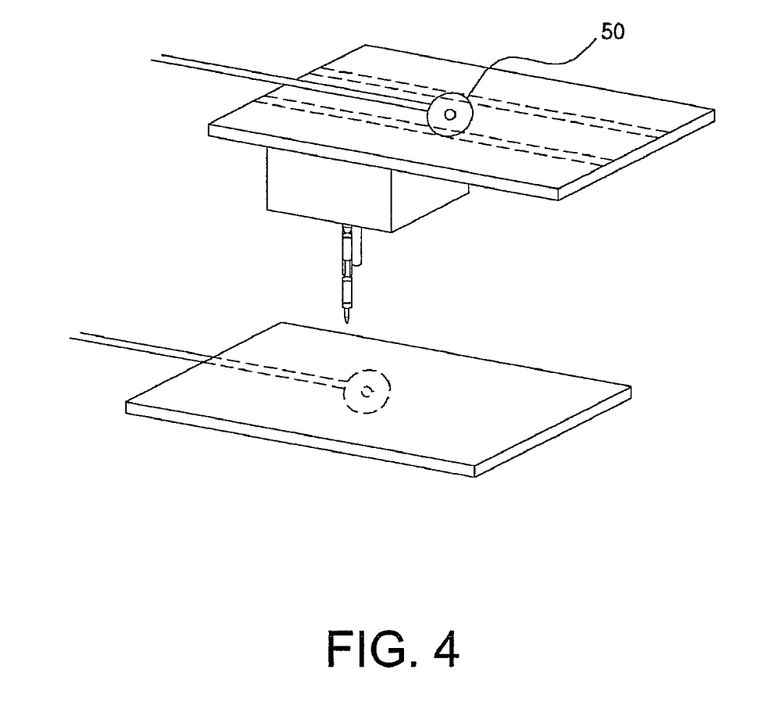
FIG. 4 is a detailed drawing illustrating a rotation part 50 coupled to a suture part 40.

To solve this problem, as described in FIG. 4, a rotation part 50 may be coupled to a suture part 40. FIG. 4 is a detailed drawing illustrating a rotation part 50 coupled to a suture part 40.

Referring to FIG. 4, a rotation part 50 may be coupled to a suture part 40 so that it may rotate within a predetermined angle range, and the suture part 40 coupled to the rotation part 50 may be configured to rotate together with the rotation part 50. Therefore, before the suture part 40 passes through a surgical port, the upper support 41 and the lower support 42 may be arranged abreast to a shaft part 20 by controlling the rotation part 50. Thereafter, the direction of the suture part 40 may be changed to be advantageous to suturing by controlling the rotation part 50 again.

Figure 5:
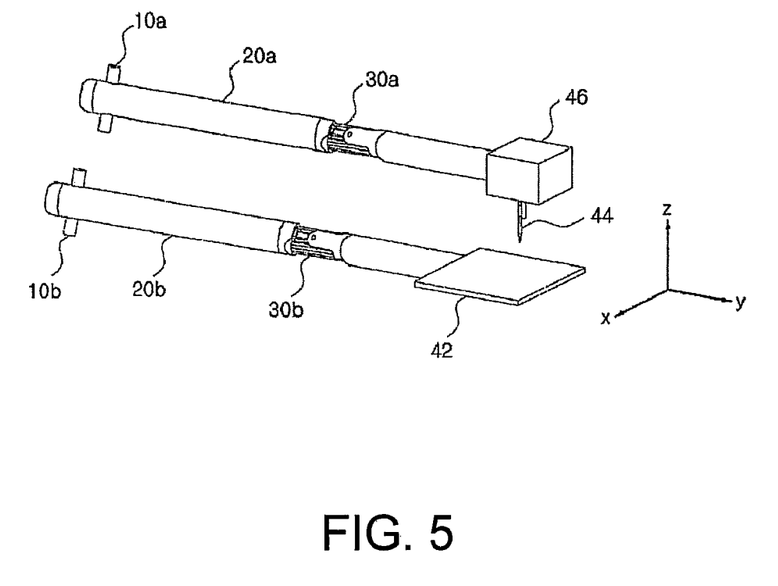
FIG. 5 is a drawing illustrating the configuration of the surgical suture apparatus in accordance with yet another embodiment of the present invention.

FIG. 5 is a drawing illustrating the configuration of the surgical suture apparatus in accordance with yet another embodiment of the present invention. According to yet another embodiment of the present invention, a surgical suture apparatus may include a first coupling part 10a, a second coupling part 10b, a first shaft part 20a, a second shaft part 20b, a first operating part 30a, a second operating part 30b, a lower support 42, a surgical needle 44 and a needle driving part 46 coupled thereto.

In accordance with the present embodiment, the upper part of a suture part 40 including the surgical needle 44 and the needle driving part 46 may be connected to the first coupling part 10a and the first shaft part 20a by way of the first operating part 30a, as described in FIG. 5, and the lower part of the suture part 40 having the lower support 42 may be connected to the second coupling part 10b and the second shaft part 20b by way of the second operating part 30b, as described in FIG. 5. Herein, the first coupling part 10a, the first shaft part 20a and the first operating part 30a may be separated from the second coupling part 10b, the second shaft part 20b and the second operating part 30b.

In accordance with the present embodiment, the joint motions while the surgical suture apparatus is being used in a human body may become freer. In other words, the first operating part 30a and the second operating part 30b of the surgical suture apparatus may take different joint motions from each other as necessary, and thus, the upper part and the lower part of the suture part 40 of the surgical suture apparatus may be controlled separately. Further, as necessary, the first operating part 30a and the second operating part 30b may be controlled by two robot arms of one surgical robot system, respectively. In this case, one robot arm may be connected to either of the first operating part 30a and the second operating part 30b to control either of the first operating part 30a and the second operating part 30b, irrespective of the shape of the first coupling part 10a or the second coupling part 10b.

In case of applying the above configurations (namely, the configurations for a separation-type surgical suture apparatus), advantageous effects as follows may be found. First, there would be no need to insert the whole surgical suture apparatus through one surgical port even when suturing the tissues of a tubular organ, and thus, it would be easier to perform a suture around the tubular organ and remove the surgical suture apparatus from the surgical port after the suture. Further, not in case of suturing the tissues of a tubular organ, it would be possible to use smaller surgical ports to insert surgical suture apparatuses when invasive surgery is done using a plurality of surgical ports. This may lead to less pain, quick recovery and minimized scars.

In accordance with a preferable embodiment of the present invention, a surgical suture apparatus may be implemented in a more sophisticated manner as follows. First, a surgical robot system for controlling a first operating part 30a and a second operating part 30b may collect the operation history of the first operating part 30a and detect the location of a first suture part 40a with regard to a reference point. Herein, it is assumed that the first suture part 40a is already located close to the tissues to be sutured, and the reference point is predetermined by the surgical robot system. Then, the surgical robot system may automatically control the second operating part 30b based on the operation history of the first operating part 30a and the location of the first suture part 40*a* so that a second suture part 40*b* may be located close to the first suture part 40*a*. And then, an operator may finely locate a lower support 42 of the second suture part 40*b* to be opposite to an upper support 41 of the first suture part 40*a*. To implement the above, well-known location control technologies may be employed by referring to the disclosures of the prior arts (e.g., the disclosure of U.S. Patent Application Publication No. 2004-143243 (Publication Date: Jul. 22, 2004)).

While embodiments of the invention has been shown and described, it will be understood by those skilled in the art that various changes and modifications may be made without departing from the spirit and the scope of the invention as defined in the following claims.

What is claimed is:

1. A surgical suture apparatus comprising:
    an upper support;
    a lower support;
    a surgical needle; and
    a needle driving part,
    wherein the upper support includes a rail,
    wherein the lower support, the surgical needle and the needle driving part form a suture part,
    wherein the surgical needle operates relative to the lower support by the needle driving part, such that a first suture thread from the surgical needle and a second suture thread from the lower support are interlaced with each other by the operation of the surgical needle,
    wherein the needle driving part is configured to move along the rail located on the upper support while facing to the lower support, and
    wherein each of the upper and the lower support and the needle driving part includes a rotation part.

2. The surgical suture apparatus as claimed in claim 1, further comprising an operating part that includes at least one joint part for providing the suture part with joint motion capability.

3. The surgical suture apparatus as claimed in claim 1, wherein the suture part performs at least one selected from a 3-layer suture, a 3-line suture, a 4-line suture, a zigzag suture, a parallel suture, a 2-needle suture, an elastic suture, a hemming suture, an embroidering, a stitching, a blind suture, an overlocking suture, and a ligaturing suture.

* * * * *